United States Patent [19]

Sarno et al.

[11] Patent Number: 5,177,194

[45] Date of Patent: Jan. 5, 1993

[54] PROCESS FOR PURIFYING IMMUNE SERUM GLOBULINS

[75] Inventors: Maria E. Sarno, Cerritos; Clifford Graf, Lake View Terrace; Gerald Neslund, Diamond Bar; Sau-Gee Yung, Rialto; James Burnham, Laverne; Jean Kim, La Canada; Rodolfo A. Vasquez, Norwalk, all of Calif.

[73] Assignee: Baxter International, Inc., Deerfield, Ill.

[21] Appl. No.: 473,559

[22] Filed: Feb. 1, 1990

[51] Int. Cl.⁵ ........................... C07K 3/12; C07K 3/28
[52] U.S. Cl. .................................. 530/412; 424/85.8;
530/386; 530/387.1; 530/388.1; 530/389.1;
530/390.1; 530/390.5; 530/414; 530/416;
530/418; 530/419; 530/420; 530/421
[58] Field of Search .................. 530/387, 387.1, 414,
530/416, 418, 419, 420, 421, 386, 388.1, 412;
424/85.8

[56] References Cited

U.S. PATENT DOCUMENTS

| | | | |
|---|---|---|---|
| 3,869,436 | 3/1975 | Falksveden | 260/122 |
| 3,962,421 | 6/1976 | Neurath | 424/89 |
| 4,314,997 | 2/1982 | Shanbrom | 424/101 |
| 4,315,919 | 2/1982 | Shanbrom | 424/177 |
| 4,540,573 | 9/1985 | Neurath et al. | 530/381 |
| 4,606,825 | 8/1986 | Crane et al. | 210/635 |
| 4,683,294 | 7/1987 | Van Wijnendaele et al. | 530/371 |
| 4,719,290 | 1/1988 | Curry et al. | 530/387 |
| 4,877,866 | 10/1989 | Rudnick et al. | 530/387 |

OTHER PUBLICATIONS

Garcia and Ornez, "The Use of Pluronic Polyols in the Precipitation of Plasma Proteins and Its Application in the Preparation of Plasma Derivatives", *Transfusion* 16:32–34 (1976).

Sober and Peterson, "Protein Chromatrophy on Ion Exchange Cellulose", *Fed Proc.* 17:1116–1126 (1958).

Polson et al., "The Fractionation of Protein Mixtures by Linear Polymers of High Molecular Weight", *Biochemica et Biophysica Acta* 82463–475 (1964).

Tayot et al., "Ion Exchange and Affinity Chromatography on Silica Derivatives" in *Methods of Plasma Fractionation* (Curling, Academic Press, London) pp. 149–160 (1980).

Zolton et al., "Removal of Hepatitis B Virus Infectivity from Human Gamma-Globulin Prepared by Ion-Exchange Chromatography", *Vox Sang* 49:381–389 (1985).

Friesen et al., "Column Ion Exchange Use", *Vox Sang* 48:201–212 (1985).

Webb, "A 30-Minute Preparative Method for Isolation of IgG from Human Serum", *Vox Sang* 23:279–290 (1972).

Stanworth, "A Rapid Method of Preparing Pure Serum Gamma-Globulin", *Nature* 488:156–157 (1960).

Bjorling, "Plasma Fractionation Methods Used in Sweden", *Vox Sang* 23:18–25 (1972).

Cohn et al., *J. Am. Chem. Soc.* 68:459–475 (1946).

*Primary Examiner*—F. T. Moezie
*Assistant Examiner*—Andrew G. Rozycki
*Attorney, Agent, or Firm*—Rothwell, Figg, Ernst & Kurz

[57] ABSTRACT

A multi-step process for purifying an immune serum globulin fraction from a crude plasma protein fraction involves precipitating non-serum globulin proteins from an aqueous suspension of the crude plasma protein fraction using a protein precipitant, adding a virus-inactivating agent to the clarified immune serum globulin-containing liquid, absorbing the immune serum globulins onto a cation exchange resin and washing non-serum globulin contaminants from the resin, subjecting the eluate to ultrafiltration to concentrate the immune serum globulins and separate them from low molecular weight species, contacting the concentrate with an anion exchange resin to absorb non-serum globulin contaminants, passing the imune-serum globulins through the anion exchange resin under conditions that leave non-serum globulin contaminants bound to the resin, and subjecting the filtrate to a molecular washing step to produce a purified immune serum globulin fraction. This process results in products substantially free of active viruses and contaminating lipids, activated complements and low molecular weight peptides. In addition, the process is advantageous in terms of efficiency and adaptability to large-scale production.

20 Claims, No Drawings

5,177,194

PROCESS FOR PURIFYING IMMUNE SERUM GLOBULINS

BACKGROUND OF THE INVENTION

This invention relates to a process for purifying immune serum globulins. More particularly, the invention relates to a process for purifying immune serum globulins from a crude plasma protein fraction.

Blood plasma proteins serve a wide variety of functions in the mammalian body. These proteins are involved in the maintenance of blood volume, viscosity, osmotic pressure, and other important physical parameters. Certain plasma proteins are themselves important biologically active molecules or act as carriers for vital nonprotein molecules. A large group of plasma proteins is concerned with the immune response. The immune serum globulins, also known as gamma globulins, include antibodies directed against many disease causative agents.

Fractionation of human plasma has long been used to produce therapeutic materials containing one or more of the plasma proteins in concentrated and purified form to achieve optimal clinical usefulness. Various fractionation schemes have been employed for recovering clinically useful proteins from human plasma. One scheme in widespread use is the well-known Cohn fractionation method, which is based on differential precipitation using cold ethanol. Cohn et al., *J. Am. Chem. Soc.*, 68, 459 (1946).

The Cohn fractionation procedure initially produces crude plasma protein fractions, which are subsequently refined to purified products.

A need exists for an efficient process for purifying an immune serum globulin fraction from a crude plasma protein fraction. Such a process should be amenable to large scale production and should inactivate any blood-carried viruses which might be present in the crude plasma fraction.

SUMMARY OF THE INVENTION

In accordance with the present invention, a process for purifying an immune serum globulin fraction from a crude plasma protein fraction is provided. This process involves the steps of: suspending the crude plasma protein fraction in water and precipitating a major proportion of the non-serum globulin proteins with a protein precipitant, recovering a clarified immune serum globulin-containing solution, adding a virus-inactivating agent to the clarified immune serum globulin-containing solution, adsorbing the immune serum globulins onto a cation exchange resin and washing non-serum globulin contaminants from the resin, eluting the immune serum globulins from the cation exchange resin and subjecting the eluate to ultra-filtration to concentrate the immune serum globulins and separate them from lower molecular weight species, contacting the concentrate with an anion exchange resin to absorb non-serum globulin contaminants, passing the immune-serum globulins through the anion exchange resin under conditions that leave non-serum globulin contaminants bound to the resin, and subjecting the filtrate to a molecular washing step to produce a purified immune serum globulin fraction.

The starting material for this process can be any crude plasma protein fraction which contains the immune serum globulins. A preferred starting material is the Cohn Fraction I+II+III. This process has been found particularly advantageous in terms of efficiency and adaptability to large-scale production. In addition, the process results in a product substantially free of active viruses and substantially free of contaminating lipids, activated complements (e.g., C5a, C3a, and the like) and low molecular weight peptides which may have adverse physiological affects.

DETAILED DESCRIPTION OF THE INVENTION

The starting material for the present process advantageously is an immune serum globulin-containing fraction from a conventional plasma fractionation process. A particularly preferred crude plasma protein fraction is the Fraction I+II+III precipitate from a large-scale Cohn fractionation procedure. This crude plasma protein fraction is usually obtained by subjecting a conventional cryoprecipitate supernatant to cold ethanol precipitation at pH 6.9. In addition to the immune serum globulins, Cohn Fraction I+II+III contains fibrinogen, various lipoproteins, several proteins involved in the hemostatic and fibrinolytic systems and numerous minor components. Although Cohn Fraction I+II+III is a preferred starting material, other starting materials may be used for the present process. Such materials include, for example, plasma, cryoprecipitate-free plasma, Cohn Fraction II+III and Cohn Fraction II.

The first step of the process involves suspending the crude plasma protein fraction in water at a substantially non-denaturing temperature and acidic pH. As used herein, "substantially non-denaturing" means that the condition to which the term refers does not cause substantial irreversible loss of biological activity of the immune serum globulins. Advantageously, the crude plasma protein fraction is suspended in cold water at volumes 5 to 10 times the weight of the fraction. The water is preferably maintained at a cold temperature which prevents substantial denaturation of the immune serum globulin proteins. Temperatures of from about 0° to about 10° C., preferably from about 1° to about 3° C. are typically employed. The suspension is acidified with a non-denaturing acid. The pH of the suspension preferably is maintained from about 4.5 to about 5.5, preferably from about 5.0 to about 5.2.

Non-serum globulin proteins are precipitated from the suspension using a protein precipitant. Substantially non-denaturing, water soluble protein precipitants are well-known in the protein purification arts. Such precipitants are used for the differential precipitation, and thus partial purification, of proteins from aqueous solutions or suspensions. Suitable protein precipitants for use in the process of the present invention include various molecular weight forms of polyethylene glycol, ammonium sulfate, polyvinylpyrrolidone and pluronics. Several grades of pluronic polyols (Pluronics ®) manufactured by the BASF Wyandotte Chemical Corporation) are effective protein precipitants. These polyols, of diversified molecular weight (from 1,000 to over 16,000) and physicochemical properties, have been used as surfactants. A family of 32 polyols with a variety of liquid, paste and solid forms is available. Pluronic F-38, of a molecular weight of 5,000, and Pluronic F-68, of molecular weight 9,000, both contain (by weight) 80 per cent hydrophilic polyoxyethylene groups and 20 per cent of hydrophobic polyoxypropylene groups. Polyethylene glycol is a preferred precipitant, particularly polyethylene glycol 3350 (PEG 3350) or polyethylene glycol 6000 (PEG 6000) (numbers represent average molecular weight of the compound).

The protein precipitant is added to the aqueous suspension in an amount sufficient to cause precipitation of a major proportion of contaminating proteins, lipids and some viruses, without causing substantial precipitation of immune serum globulins. The protein precipitant may be added to the crude plasma protein suspension as a solid, or an aqueous concentrate derived from the commercially available solid powder or flakes. The actual amount of protein precipitant used will vary, depending upon the particular precipitant employed, the temperature, pH and protein concentration in the suspension. When PEG 3350 is used, final concentrations of the precipitant in the aqueous suspension advantageously range from about 3% to about 20% by weight, preferably from about 6% to about 12% by weight. The precipitation is allowed to proceed until equilibrium is reached, e.g., generally for about one hour or more. The suspension preferably is maintained at a low temperature (e.g., less than about 10° C, preferably less than about 5° C.) throughout the precipitation step.

Following precipitation, a clarified immune globulin-containing liquid is recovered from the solids-liquid mixture resulting from the precipitation. Recovery of the clarified liquid can be accomplished by conventional solids-liquid separation techniques, such as centrifugation and filtration. Preferably, a centrifuge with at least about 5,000 G force or a tangential flow filter system with micro filtration membranes is employed.

Infectious viruses that may still be present in the crude plasma protein fraction can be inactivated at this stage of the procedure. Such inactivation is accomplished by adding a virucidal amount of a virus-inactivating agent to the clarified immune serum globulin-containing liquid. Preferred virus-inactivating agents are detergents, most preferably, detergent-solvent mixtures. A wide variety of detergents can be used for virus inactivation. Suitable detergents are described, for example, by Shanbrom et al , in U.S. Pat. Nos. 4,314,997, 4,315,919, and 4,540,573, the disclosures of which are incorporated herein by reference. Preferred detergents are oxyethylated alkylphenols, such as those sold by the Rohm & Haas Company under the trademark, Triton X-100, and polyoxyethylated derivatives of a partial ester of a $C_{12-22}$ fatty acid and a hexatol anhydride, such as those sold under the trademark Tween 80. Preferred solvents for use in virus-inactivating agents are the lower alkyl esters of phosphoric acid, as described, for example, by Neurath in U.S. Pat. No. 3,962,421, the disclosure of which is incorporated herein by reference. A particularly preferred solvent is tri(n-butyl) phosphate. A preferred virus-inactivating agent for the practice of the present invention is a mixture of tri(n-butyl) phosphate, Triton X-100 and Tween 80. The mixture is formulated and used such that the concentration of tri(n-butyl) phosphate in the clarified immune serum globulin-containing liquid ranges from about 0.2 to about 0.4% by weight, the concentration of the Triton X-100 ranges from about 0.7 to about 1.3% by weight, and the concentration of the Tween 80 ranges from about 0.2 to about 0.4% by weight.

The virus-inactivating step is conducted under virus-inactivating conditions. In general, such conditions include a temperature of from about 10° C. to about 30° C., preferably from about 18° C. to about 22° C. and an incubation time found to be effective by experimentation. Generally, an incubation time of about one hour is sufficient.

After virus inactivation, the solution is contacted with a cation exchange resin to remove the virus-inactivating agent and other non-serum globulin contaminants. This step is preferably conducted by passing the solution over a column packed with a cation exchange resin, such as carboxymethyl agarose. The column preferably is equilibrated with a buffer which converts the resin to the salt form. A preferred buffer is an acetate buffer having an acetate concentration ranging from about 5 to about 50 millimolar, preferably from about 10 to about 20 millimolar. Suitable acetate buffers may be prepared from sodium acetate trihydrate and glacial acetic acid, and have a pH ranging from about 5 to 6. Another preferred buffer is a phosphate buffer having a pH of 5 to 6.

Prior to loading the immune serum globulin-containing liquid onto the column, the salt concentration of that liquid preferably is adjusted to an amount substantially equivalent to the salt concentration of the equilibration buffer. For example, if an acetate buffer is used for the acetate concentration in the immune serum globulin-containing liquid is adjusted to approximately the same concentration as that in the buffer. After loading the immune serum globulin-containing liquid onto the column, the column is advantageously washed sequentially with the same buffer used for equilibration. A preferred procedure involves employing sequential washes with decreasing concentrations of the virus-inactivating agents, with a final wash of at least ten times the bed volume of the column with a buffer devoid of the virus-inactivating agent. Sequential washes are advantageous in reducing resin-bound lipids while also removing the virus-inactivating agents from the cation exchange resin. Sequential washing has also been found to reduce pre-kallikrein activator, thus resulting in a final product substantially free of this protein. For example, after loading the column, it is washed with at least two times its bed volume with a 10 mM acetate buffer, pH 5.0-6.0, containing 1% Triton X-100 and 0.3% Tween 80, or a 10 mM acetate buffer, pH 5.0-6.0, containing 1% Triton X-100. This washing may be followed by washing with at least four times the column bed volume with a 10 mM acetate buffer, pH 5.0-6.0, containing 1% Tween 80 until the absorbance at 280 nM is less than about 1.2. When the $A_{280}$ has decreased below 1.2, the column advantageously is washed with at least 20 times its bed volume with 10 mM acetate buffer, pH 5.0-6.0.

The immune serum globulins are eluted from the cation exchange resin with a substantially non-denaturing buffer having a pH and ionic strength sufficient to cause substantial elution of the immune serum globulins. In general, the pH of the eluting buffer is in the basic range, preferably from about 7.0 to about 8.5. The salt concentration of the eluting buffer is relatively high to displace the immune serum globulin proteins from the resin. A preferred buffer contains about 25 mM tris(hydroxymethyl)aminomethane, about 0.25M sodium chloride, about 0.1% polyethylene glycol and about 0.2M glycine at pH 8.0. The polyethylene glycol and glycine combination serves to stabilize the protein during the elution step. Numerous other buffer systems may be used for eluting the immune serum globulins, as will be appreciated by those skilled in the art.

Following elution from the cation exchange column, the eluate is advantageously concentrated by ultrafiltration. The extent of concentration may vary considerably. Concentrating the solution to about 1 to about 3% by weight protein, preferably from about 1.5 to about 2.5% protein has been found satisfactory. The ultrafiltration membranes employed advantageously have a molecular weight cut-off ranging from about 10,000 to about 100,000. A particularly preferred membrane for the present process is a PTHK polysulfone membrane with a nominal molecular weight cut-off of 100,000, obtained from Millipore Corp. Other commercially available ultrafiltration membranes of comparable porosity may be employed. Following concentration, the concentrate is advantageously molecular washed using the same ultrafiltration system. This step effectively removes low molecular weight peptide contaminants and provides a means for buffer exchange required for the next purification step. A preferred solution for the molecular washing step is an aqueous solution containing from about 0.005 to about 0.012% by weight polyethylene glycol. The polyethylene glycol serves to stabilize the protein.

The molecular washing is continued until the salt concentration of the ultrafiltrate is reduced to a point that the solution conductivity of less than about 5 mMHO/cm. preferably less than about 3 mMHO/cm.

The pH of the concentrated solution is adjusted to a substantially non-denaturing basic pH, e.g., from about 7.0 to about 8.5. The concentrate is then contacted with an anion exchange resin to absorb non-serum globulin contaminants. This step is advantageously conducted by passing the concentrate over a column packed with an anionic exchange resin, such as diethylaminoethyl-sepharose ("DEAE-SEPHAROSE"). The anion exchange column is first equilibrated with a basic buffer which converts it to the chloride form. Any of a variety of buffers can be employed, and a preferred buffer is 25 mM tris(hydroxymethyl)aminomethane, 20 mM sodium chloride, pH 8.0. Those skilled in the art will appreciate that numerous other buffers may be used for equilibration. Prior to loading the immune serum globulin concentrate onto the resin, it may be prefiltered to ensure that the solution is free of particulate matter.

The immune serum globulin concentrate is loaded onto the column. Most of the serum immune globulins flow unadsorbed through the column and effective recovery is accomplished by washing with at least two times the bed volume of the same buffer used for equilibration. The immune serum globulin containing fractions are collected and combined and the pH is adjusted to a substantially non-denaturing acidic pH. The purified immune serum globulin solution is again concentrated by an ultrafiltration step, which also removes salts and low molecular weight contaminating species. Additional molecular washing steps may be performed substantially as described above. These steps result in a highly purified immune serum globulin fraction.

The process of this invention offers a number of advantages over processes described in the prior art. It is a relatively fast procedure and avoids the need of further purifying crude plasma protein fractions, such as Cohn Fraction I+II+III to Cohn Fraction II for use as starting material for obtaining therapeutic products. In addition, the process is efficient in terms of labor and yield. For example, it usually takes 4-5 days to process Cohn Fraction I+II+III to Cohn Fraction II using the Cohn process. An additional 2-3 days are required to purify Cohn Fraction II to an acceptable product. Using the process of the present invention, a high quality immune serum globulin product can be obtained in 3-4 days. Moreover, the product resulting from this process has reduced low molecular weight peptides which may have adverse physiological effects. The present process also provides better immune globulin yields than conventional procedures starting with Cohn Fraction II. Another advantage of the process is its amenability to large scale production.

A particular advantage of the process is that it removes components of the crude plasma protein fraction which might be deleterious to patients receiving therapeutic amounts of the immune serum globulin fraction. Viruses such as Hepatitis B and HIV are inactivated. Contaminating lipids and activated complement components, such as C5a, C3a, etc., are also reduced to very low levels.

The invention is further illustrated by the following examples, which are not intended to be limiting.

EXAMPLE

Cohn Fraction I+II+III was suspended in ten (10) volumes of water at about 2° C. The pH was adjusted to about 5.0 with 1M acetic acid. After the pH stabilized, a 50% polyethylene glycol 3350 ("PEG 3350") solution was added to the aqueous suspension in an amount sufficient to produce a PEG 3350 concentration of 8% in the resulting suspension. The suspension was mixed completely and precipitation was permitted to proceed for one hour at a temperature of about 2° C. The resulting precipitate and undissolved paste was separated by centrifugation at 5000 g force or by filtration. The precipitate was discarded and the supernate was clarified by filtration. The clarified solution was then brought to ambient temperature (22° C.) prior to the addition of detergents. Solvent/detergent was added to the solution in an amount sufficient to result in a final concentration by weight of solution of 1% Triton X-100, 0.3% Tween-80, and 0.3% tri-n-butyl-phosphate (TNBP). The detergent-treated solution was permitted to incubate for one (1) hour at 22° C. to permit viral inactivation.

After the incubation period, the acetate concentration of the treated solution was adjusted to 10 mM. The detergent and some protein contaminants were separated from the immune serum globulin by absorption of the latter to a cation exchange resin. The acetate-adjusted, detergent-treated solution was loaded onto a CM-Sepharose Fast Flow column which had been previously equilibrated with 10 mM acetate buffer solution, pH 5.5. Detergent and protein impurities were washed from the protein-bound resin with 2× the bed volume of a 10 mM acetate buffer, pH 5.5, containing 1% by weight Triton X-100 and 0.3% by weight Tween-80. This was followed by washing with 4× the bed volume with 10 mM acetate buffer, pH 5.5, containing 1% by weight Tween-80, until the optical density at 280 nm. of the spent wash solution was less than 1.2. This was then followed by washing with 20x the bed volume with 10 mM acetate buffer, pH 5.5.

Following the washing steps, the bound immune serum globulin was eluted from CM-Sepharose Fast Flow column with a buffer solution of 25 mM tris(hydroxymethyl)aminomethane ("tris"), 0.25M NaCl, 0.1% by weight PEG 3350, and 0.2 M glycine at pH 8.0. The pH of the eluate was adjusted to 5.2. Then the eluate was concentrated to approximately 2% by weight of protein using an ultrafiltration ("UF") system with PTHK membranes (polysulfone membranes with nominal molecular weight cut-off of 100,000). The concentrate was molecular washed and diafiltered using the same UF system with 0.008% by weight PEG 3350, until the conductivity was below 2 mMHO/cm. The pH of the solution was adjusted to 8.0 with 2 M tris, pH 8.4, and the clarified solution was adsorbed through an anionic DEAE-Sepharose Fast Flow column, which had been previously equilibrated with a buffer containing 25 mM tris and 20 mM NaCl at pH 8.0. The void-volume of non-adsorbed solution (DEAE-filtrate) containing immune serum globulin was collected. To recover entrapped immune serum globulin, the DEAE column was then washed with 2× the bed volume with the same buffer as previously used for equilibration, containing 25 mM tris, 20 mM NaCl at pH 8.0. The postwash was added to the DEAE filtrate. The pH was adjusted to 5.2 with 1M citric acid or equivalent and diafiltered with a 0.005% PEG solution if necessary until low molecular weight activated complement proteins could no longer be detected using conventional RIA methods. The glycine concentration of the solution was adjusted to 0.2 M and made isotonic with sodium citrate. The solution was then concentrated to 10%. The 10% solution was stabilized with a final concentration of 0.007% Tween-80, sterile filtered, and filled into appropriate containers.

We claim:

1. A process for purifying an immune serum globulin fraction from a crude plasma protein fraction, which comprises the steps of:
    (a) providing an aqueous suspension of a crude plasma protein fraction at a substantially non-denaturing temperature and acidic pH, wherein the protein concentration in the aqueous suspension is sufficient that, during the following precipitation step, non-serum globulin proteins precipitate while retaining immune serum globulins in said suspension;
    (b) adding a water soluble, substantially non-denaturing protein precipitant to the aqueous suspension of step (a) at a concentration sufficient to cause precipitation of non-serum globulin proteins, while retaining immune serum globulins in said suspension, thereby forming a solid-liquid mixture;
    (c) recovering a clarified immune serum globulin-containing liquid from the solid-liquid mixture of step (b);
    (d) adding a virucidal amount of a virus-inactivating agent to the clarified immune serum globulin-containing liquid of step (c) so as to inactive any viruses therein;
    (e) contacting the virus-inactivated immune serum globulin-containing liquid with a cation exchange resin and washing non-serum globulin contaminants from the resin with a buffer having a pH and ionic strength sufficient to eliminate the virus-inactivating agent and other non-serum globulin contaminants from the resin while retaining immune serum globulins in said liquid;
    (f) eluting immune serum globulins from the cation resin with a substantially non-denaturing buffer having a pH and ionic strength sufficient to cause immune serum globulin elution, thereby forming an immune serum globulin-containing eluate;
    (g) subjecting the immune serum globulin-containing eluate to ultrafiltrations for concentrating immune serum globulins from said eluate and separating them from species having lower molecular weights, thereby forming an immune serum globulin concentrate;
    (h) adjusting the pH of the immune serum globulin concentrate to a substantially non-denaturing basic pH, thereby forming a basic immune serum globulin concentrate;
    (i) contacting the basic immune serum globulin concentrate with an anion exchange resin to bind the contaminating proteins as a means of separating said contaminating protein from the unbound immune serum globulin, thereby forming an immune serum globulin enriched solution; and
    (j) adjusting the pH of the immune serum globulin enriched solution to a non-denaturing acidic pH and molecular washing the acidified solution using an ultrafiltration membrane which retains immune serum globulins and which possess contaminating species having molecular weights lower than those of the immune serum globulins, thereby producing a purified immune serum globulin fraction.

2. The process of claim 1, wherein the suspension in step (a) contains from about 5 to about 10 parts by volume water per part by weight of the crude plasma protein fraction, wherein the temperature of the aqueous suspension is maintained from about 0° to about 5° C., and the pH of the aqueous solution is maintained from about 4.5 to about 5.5.

3. The process of claim 2, wherein the protein precipitant employed in step (b) is polyethylene glycol, ammonium sulfate, polyvinylpyrrolidone or pluronics.

4. The process of claim 3, wherein the protein precipitant is PEG 3350 or PEG 6000.

5. The process of claim 3, wherein the virus-inactivating agent is a detergent.

6. The process of claim 3, wherein the virus-inactivating agent is a mixture of a non-denaturing detergent and a tri(lower alkyl) phosphate solvent.

7. The process of claim 6, wherein the detergent is selected from the group consisting of non-ionic, cationic and anionic detergents.

8. The process of claim 3, wherein the virus-inactivating agent is a mixture of tri(n-butyl)phosphate, an oxyethylated alkylphenol, and a polyoxyethylated derivative of a partial ester of a $C_{12}$–$C_{22}$ fatty acid and a hexitol anhydride, wherein the concentration of the tri(n-butyl)phosphate in the clarified immune serum globulin-containing liquid is from about 0.1 to about 0.5% by weight, the concentration of the oxyethylated alkylphenol in the clarified immune serum globulin-containing liquid is from about 0.5 to about 2% by weight and the concentration of the polyoxyethylated derivative of a partial ester of a $C_{12}$–$C_{22}$ fatty acid and a hexitol anhydride in the clarified immune serum globulin-containing liquid is from about 0.1 to about 0.5% by weight.

9. The process of claim 8, wherein the concentration of the tri(n-butyl)phosphate in the clarified immune serum globulin-containing liquid is from about 0.2 to about 0.4% by weight, the concentration of the oxyethylated alkylphenol in the clarified immune serum globulin-containing liquid is from about 0.7 to about 1.3% by weight and the concentration of the polyoxyethylated derivative of a partial ester of a $C_{12}$–$C_{22}$ fatty acid and a hexitol anhydride in the clarified immune serum globulin-containing liquid is from about 0.2 to about 0.4% by weight.

10. The process of claim 6, wherein the cation exchange resin contains carboxymethyl groups.

11. The process of claim 10, wherein the non-serum globulin contaminants are eluted in step (e) with an acetate buffer having an acetate concentration of from about 5 to about 50 millimolar.

12. The process of claim 10, wherein the non-serum globulin contaminants are eluted in step (e) sequentially with an acetate buffer having an acetate concentration of from about 5 to about 50 millimolar acetate, a pH from about 5.0 to about 6.0 and decreasing concentrations of the virus-inactivating agent, with a final wash of at least about 10 times the bed volume of the cation exchange resin with said acetate buffer which is devoid of the virus-inactivating agent.

13. The process of claim 10, wherein immune serum globulins are eluted from the cation exchange resin with a buffer solution having a pH of from about 7.0 to about 8.5.

14. The process of claim 13, wherein the buffer solution contains tris(hydroxymethyl-)aminomethane at a concentration of from about 20 to about 30 millimolar, sodium chloride at a concentration of from about 0.2 to about 0.3 molar, from about 0.05 to about 0.2% polyethylene glycol and from about 0.1 to about 0.3M glycine.

15. The process of claim 1, wherein the ultrafiltration of step (g) is conducted with a membrane having a molecular weight cut-off of from about 10,000 to about 100,000.

16. The process of claim 15, which further comprises molecular washing the immune serum globulin-containing eluate with an aqueous solution which contains from about 0.001 to about 0.012% by weight polyethylene glycol until the conductivity of the ultrafiltrate is at least as low as about 2 mMHO/cm.

17. The process of claim 1, wherein the anion exchange resin contains diethylaminoethyl groups.

18. The process of claim 17, wherein unbound immune serum globulins are passed through the anion exchange resin with a buffer solution having a pH of from about 7.0 to about 8.5.

19. The process of claim 18, wherein the buffer solution contains tris(hydroxymethyl)aminomethane at a concentration of from about 20 to about 30 millimolar and sodium chloride at a concentration of from about 10 to about 30 millimolar.

20. The process of claim 1, wherein, in step (j), the pH of the purified immune serum globulin solution is adjusted to about 4.5 to about 6.0, and the molecular washing is conducted with an ultrafiltration membrane having a molecular weight cut-off of from about 10,000 to about 120,000.

* * * * *

UNITED STATES PATENT AND TRADEMARK OFFICE
CERTIFICATE OF CORRECTION

PATENT NO.   : 5,177,194
DATED        : January 5, 1993
INVENTOR(S)  : Maria E. C. Sarno et al.

It is certified that error appears in the above-identified patent and that said Letters Patent is hereby corrected as shown below:

**On cover page, item [75] change "Maria E. Sarno" to
   --Maria E. C. Sarno--.**

Col. 9, line 20, "hydroxymethyl-)" should be --hydroxymethyl)--.

Signed and Sealed this

Eighth Day of November, 1994

Attest:

BRUCE LEHMAN

*Attesting Officer*    *Commissioner of Patents and Trademarks*